United States Patent
Stein et al.

(10) Patent No.: US 6,447,922 B1
(45) Date of Patent: Sep. 10, 2002

(54) CURABLE SILICON ADHESIVE COMPOSITIONS

(75) Inventors: Judith Stein, Schenectady; Christina Marie Darkangelo Wood, Scotia, both of NY (US); Eriny Demian Youssef, East Brunswick, NJ (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/716,617

(22) Filed: Nov. 20, 2000

(51) Int. Cl.$^7$ ............................ B32B 9/04; C08G 77/18
(52) U.S. Cl. .................. 428/447; 427/387; 528/15; 528/31; 524/588
(58) Field of Search .................. 528/15, 31; 524/588; 427/387; 428/447

(56) References Cited

U.S. PATENT DOCUMENTS

| | | |
|---|---|---|
| 2,938,009 A | 5/1960 | Lucas |
| 3,159,601 A | 12/1964 | Ashby et al. |
| 3,159,662 A | 12/1964 | Ashby |
| 3,220,970 A | 11/1965 | Carlstrom et al. |
| 3,516,946 A | 6/1970 | Modic et al. |
| 3,635,743 A | 1/1972 | Smith |
| 3,775,452 A | 11/1973 | Karstedt |
| 3,814,730 A | 6/1974 | Karstedt |
| 3,847,848 A | 11/1974 | Beers |
| 4,029,629 A | 6/1977 | Jeram |
| 4,061,609 A | 12/1977 | Bobear |
| 4,273,698 A * | 6/1981 | Smith, Jr. et al. ....... 260/37 SB |
| 5,414,066 A | 5/1995 | Stein et al. |
| 6,004,679 A * | 12/1999 | Mitchell et al. ............ 428/446 |

* cited by examiner

Primary Examiner—Margaret G. Moore
(74) Attorney, Agent, or Firm—Bernadette M. Bennett; Noreen C. Johnson

(57) ABSTRACT

A silicone composition is provided which comprises a room-temperature vulcanizable adhesive formulation which comprises at least one bis(trialkoxysilylalkyl)succinate, a vinyl-containing polydiorganosiloxane, a hydrogen-containing polysiloxane, and a catalytic amount of a hydrosilylation catalyst.

38 Claims, No Drawings

CURABLE SILICON ADHESIVE COMPOSITIONS

The government has rights in this invention pursuant to Contract No. DAAE3099C1042 awarded by SERDP.

BACKGROUND OF THE INVENTION

The present invention is related to curable silicone compositions. More specifically, the present invention is related to room temperature vulcanizable (RTV) adhesive formulations which provide adhesion to substrates.

Curable silicone compositions are used as laminates over a variety of substrates and in a wide variety of applications. In order to impart self-bonding adhesive properties to the silicone composition such that a primer is not needed between the silicone composition and a substrate, adhesion promoters in the silicone composition are commonly used.

Mitchell et al., U.S. Pat. No. 5,164,461, discuss an addition-curable silicone composition which includes a vinyl-containing polydiorganosiloxane, a hydrogen-terminated polysiloxane, and an adhesion promoter. The adhesion promoters include silylmaleates, silylmaleimides and silylfumarates. The silicone composition is useful for self-bonding to substrates such as plastics, metals, and glass at a cure temperature in a range between about 100° C. and about 150° C. The silicone composition disclosed has both excellent physical properties and excellent lap shear adhesive properties.

Stein et al., U.S. Pat. No. 5,414,066, is directed to a room-temperature addition-curable silicone adhesive composition which incorporates N-heterocyclic silanes as the adhesion promoter. The addition of the N-heterocyclic silane to a vinyl-containing polydiorganosiloxane and a hydrogen-terminated polysiloxane provides a silicone adhesive composition which cures at room temperature. The composition is directed to providing adhesion to substrates such as glass, plastics and metals.

Although silicone adhesive compositions which have the ability to cure at room temperature have been developed which provides adhesion to plastic and metal substrates, silicone adhesive compositions with new adhesion promoters are constantly being sought which can both cure at room temperature and include desired physical properties.

BRIEF SUMMARY OF THE INVENTION

The present invention relates to a silicone composition which comprises a room temperature vulcanizable adhesive formulation which comprises:
(A) at least one bis(trialkoxysilylalkyl)succinate,
(B) a vinyl-containing polydiorganosiloxane,
(C) a hydrogen-containing polysiloxane, and
(D) a catalytic amount of a hydrosilylation catalyst.

A further embodiment of the present invention is a method to provide cohesive failure to a silicone composition and a substrate which comprises the steps of:
(I) applying a silicone composition to a substrate wherein the silicone composition comprises:
(A) at least one bis(trialkoxysilylalkyl)succinate,
(B) a vinyl-containing polydiorganosiloxane,
(C) a hydrogen-containing polysiloxane, and
(D) a catalytic amount of a hydrosilylation catalyst, and
(II) curing the silicone composition.

A further embodiment of the present invention provides a bis(trialkoxysilylalkyl)succinate which comprises the formula

wherein $R^3$ and $R^1$ independently at each occurrence is hydrogen, an alkyl radical, aryl radical, aralkyl radical, alkaryl radical, cycloalkyl radical, or bicycloalkyl radical; $R^2$ comprises hydrogen or an alkyl radical; and "x" is in a range between about 3 and about 8.

DETAILED DESCRIPTION OF THE INVENTION

It has been found that the incorporation of an effective amount of a bis(trialkoxysilylalkyl)succinate as an adhesion promoter into silicone compositions provides a room temperature vulcanizable (RTV) adhesive formulation which adheres to metal substrates and polymer substrates. An "effective amount of a bis(trialkoxysilylalkyl)succinate" as used herein is an amount of the adhesion promoter which promotes adhesion to metal and polymer substrates. Preferably, the amount of adhesion promoter is in a range between about 0.1% by weight and about 5% by weight of the total room temperature vulcanizable adhesive formulation, herein referred to as "total composition" or "silicone composition".

The adhesion promoter is (A) at least one bis(trialkoxysilylalkyl)succinate which usually has the general formula (I):

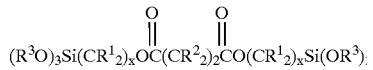

wherein "x" has a value in a range between about 3 and about 8. Each $R^3$ and $R^1$ independently represents hydrogen or a monovalent hydrocarbon group such as alkyl radicals, aryl radicals, aralkyl radicals, alkaryl radicals, cycloalkyl radicals, or bicycloalkyl radicals. Each $R^2$ represents hydrogen or an alkyl radical. The term "alkyl radical" is intended to designate both normal alkyl and branched alkyl radicals. Normal and branched alkyl radicals are preferably those containing carbon atoms in a range between about 1 and about 20, and include as illustrative non-limiting examples methyl, ethyl, propyl, isopropyl, butyl, tertiary-butyl, pentyl, neopentyl, hexyl, octyl, decyl, dodecyl. Aryl radicals include examples such as phenyl and tolyl. Cyclo- or bicycloalkyl radicals represented are preferably those containing ring carbon atoms in a range between about 3 and about 12 with a total number of ring carbon atoms less than or equal to about 50. Some illustrative non-limiting examples of these cycloalkyl radicals include cyclobutyl, cyclopentyl, cyclohexyl, methylcyclohexyl, and cycloheptyl. Preferred aralkyl radicals are those containing carbon atoms in a range between about 7 and about 14; these include, but are not limited to, benzyl, phenylbutyl, phenylpropyl, and phenylethyl. Most preferably, a bis(trimethoxysilylpropyl)succinate is used as the adhesion promoter wherein $R^3$ comprises an alkyl radical with 1 carbon atom, $R^1$ comprises hydrogen, $R^2$ comprises hydrogen, and "x" is 3.

The bis(trialkoxysilylalkyl)succinate of the present invention can be synthesized by first effecting a reaction between diallylsuccinate and a hydrosilylation catalyst, for example, a platinum catalyst to form a succinate-catalyst mixture. The resulting succinate-catalyst mixture is then reacted with trialkoxysilane to form the bis(trialkoxysilylalkyl)succinate.

In addition to the effective amount of at least one bis(trialkoxysilylalkyl)succinate (A), the room temperature vulcanizable adhesive formulation includes (B) a vinyl-containing polydiorganosiloxane, (C) a hydrogen-containing polysiloxane, and (D) a catalytic amount of a hydrosilylation catalyst.

The vinyl-containing polydiorganosiloxane has the general formula (II), $$(R^4)_2R^5SiO[(R^4)_2SiO]_m[R^4R^5SiO]_nSi(R^4)_2R^5 \quad (II)$$

wherein $R^5$ is an ethylenic unsaturated radical, preferably vinyl; $R^4$ is selected from the group consisting of $C_{1-8}$ alkyl radicals, phenyl radicals, and $C_{3-10}$ fluoroalkyl radicals and mixtures thereof, "m"+"n" has a value sufficient to provide a total vinyl-containing composition with a viscosity in a range between about 100 centipoise and about 100,000 centipoise at 25° C., and preferably, in a range between about 3000 centipoise and about 95,000 centipoise at 25° C. and a vinyl content in a range between about 0.02% by weight and about 2.0% by weight of the vinyl-containing polydiorganosiloxane. Radicals represented by $R^4$ are preferably $C_{1-4}$ alkyl radicals and more preferably, methyl. Typically, the vinyl-containing polydiorganosiloxane is present in a range between about 10% by weight and about 50% by weight of the total composition.

The vinyl-containing polydiorganosiloxane (B) includes (1) the vinyl-containing polydiorganosiloxane and may also include (2) a vinyl-containing siloxane resin copolymer.

The vinyl-containing siloxane resin copolymer is present in a range between about 0% by weight and about 70% by weight of the total composition having $$(R^6)_3SiO_{1/2} \text{ units ("M") and } SiO_{4/2} \text{ units ("Q")},$$

wherein $R^6$ is a vinyl radical, or a monovalent hydrocarbon radical free of aliphatic unsaturation and containing no more than six carbon atoms, the ratio of $(R^6)_3SiO_{1/2}$ units to $SiO_{4/2}$ units being in a range between about 0.5:1 and about 1.5:1, and the resin having a vinyl content in a range between about 1.5% by weight and about 3.5% by weight of the vinyl-containing siloxane resin copolymer. The vinyl-containing siloxane resin copolymer is also referred to as the "vinyl-containing MQ resin" or "$M^{Vi}Q$".

The vinyl-containing siloxane resin copolymer may further contain (i) $R^6SiO_{3/2}$ units ("T"), (ii) $(R^6)_2SiO_{2/2}$ units ("D"), or combinations thereof, where the $(R^6)_2SiO_{2/2}$ units are present in an amount in a range between about 0 mole percent and about 10 mole percent based on the total number of moles of siloxane units in the vinyl-containing siloxane resin copolymer and $R^6$ is as defined above.

The hydrogen-containing polysiloxane (C) functions as a cross-linking agent and is typically present in a range between about 1% by weight and about 15% by weight of the total composition. The hydrogen-containing polysiloxane is represented by an average unit formula (III), $$R^7_dH_eSiO_{(4-d-e)/2}$$

wherein $R^7$ is hydrogen, a monovalent hydrocarbon radical, or halogenated monovalent hydrocarbon radical having carbon atoms in a range between about 1 and about 10, and free of aliphatic unsaturation, "d" has a value in a range between 0 and about 3, "e" has a value in a range between about 1 and about 3, and the sum of "d"+"e" has a value in a range between about 1 and about 3. $R^7$ is preferably selected from $C_{1-8}$ alkyl radicals, phenyl, $C_{3-10}$ fluoroalkyl radicals, and hydrogen and most preferably, methyl. Most typically, the preferred fluoroalkyl radical is trifluoropropyl.

A preferred hydrogen-containing polysiloxane has the formula (IV)

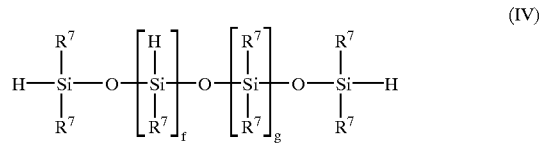

(IV)

where $R^7$ is as defined above, "f" and "g" have values which are sufficient when added together to provide a viscosity in a range between about 10 centipoise and about 1000 centipoise at 25° C., and preferably, in a range between about 10 centipoise and about 150 centipoise at 25° C., and the reactive hydrogen content is in a range between about 0.02% by weight and about 1.6% by weight of the hydrogen-containing polysiloxane. The hydrogen-containing polysiloxane of formula (IV) can be used as a hydride cross-linking agent in the present invention.

Other hydrogen-containing polysiloxanes which can be used in the present invention include siloxane copolymer resins comprised of "M" units which comprise $(R^7)_3SiO_{1/2}$, "$M^H$" units which comprise $H(R^7)_2SiO_{2}$, "D" units which comprise $(R^7)_2SiO_{2/2}$, "$D^H$" units which comprise $HR^7SiO_{2/2}$, "T" units which comprise $R^7SiO_{3/2}$, "$T^H$" units which comprise $HSiO_{3/2}$, and "Q" units, and mixtures thereof wherein the mixtures comprise at least one hydrogen. The preferred resins are known as $M^HQ$ resins, which comprise diorganohydrogensiloxy units ($M^H$) and $SiO_{4/2}$ units (Q) wherein the ratio of diorganohydrogensiloxy units to Q units is in a range between about 0.4:1.0 and about 2.0:1.0 inclusive. Hydrogen-containing polysiloxanes having at least one $R^7$ group, preferably, a methyl group, bonded to silicon which bears at least one reactive hydrogen atom are preferred. It is understood that the hydrogen-containing polysiloxane can be a single compound or a mixture of compounds. Additional hydrogen-containing polysiloxanes suitable for use in the present invention are described, for example, in U.S. Pat. No. 4,061,609.

The room temperature vulcanizable adhesive formulation further contains a catalytic amount of a hydrosilylation catalyst (D). The hydrosilylation catalyst (E) promotes the hydrosilylation reaction. The hydrosilylation catalyst (D) typically is a platinum group metal catalyst. Additional catalysts for facilitating the hydrosilylation curing reaction include precious metal catalysts such as those containing ruthenium, rhodium, palladium, osmium, or iridium, or complexes of these metals. Examples of suitable hydrosilylation catalysts for use in the present invention are disclosed, for example, in U.S. Pat. Nos. 3,159,601 and 3,159,662; 3,220,970; 3,814,730; 3,516,946; and 4,029,629.

The hydrosilylation catalyst is preferably a platinum-containing catalyst. Preferably, the platinum-containing catalyst is a platinum complex formed by reacting chloroplatinic acid containing about 4 moles of water of hydration with tetravinylcyclotetrasiloxane in the presence of sodium bicarbonate in an ethanol solution. This catalyst is disclosed in U.S. Pat. No. 3,775,452 and is often referred to as Karstedt's catalyst.

The hydrosilylation catalyst is used in a catalytic amount, which is an amount sufficient to promote the hydrosilylation reaction. Generally, there is utilized at least about 0.1 part per million (ppm) of a platinum catalyst, and preferably in a range between about 5 parts per million and about 250 parts per million, in terms of parts of platinum metal based on the weight of total composition.

Inhibitors such as acetylenic alcohols (e.g., 3,5 dimethyl-1-hexyn-3-ol and 2 methyl-3-butyn-2-ol), amines, and tetravinyltetramethylcyclotetrasiloxane and mixtures thereof can also be employed when used in an effective amount which is typically in a range between about 0.01% by weight and about 1% by weight of the total composition.

The room temperature vulcanizable adhesive formulation of the present invention may also contain any of the conventional extending fillers (E), reinforcing fillers (F), and mixtures thereof. The room temperature vulcanizable adhesive formulation contains extending filler in a range between about 0% by weight and about 50% by weight, and preferably in a range between about 10% by weight and about 30% by weight of the total composition, and reinforcing filler in a range between about 0% by weight and about 70% by weight, and preferably in a range between about 20% by weight and about 50% by weight of the total composition.

Examples of extending fillers (E) useful herein include alpha quartz, crushed quartz, aluminum oxide, aluminum silicate, zirconium silicate, magnesium oxide, zinc oxide, talc, diatomaceous earth, iron oxide, calcium carbonate, clay, titania, zirconia, mica, glass, such as ground glass or glass fiber, sand, carbon black, graphite, barium sulfate, zinc sulfate, wood flour, cork, fluorocarbon polymer powder and the like. Alpha quartz is the most preferred extending filler.

Examples of reinforcing fillers (F) include silica, such as fumed silica or precipitated silica, and treated silica fillers such as fumed or precipitated silica that has been reacted with, for example, an organohalosilane, a disiloxane, or a disilazane. Fumed silica is particularly effective as a reinforcing filler for the compositions of the present invention. A particularly preferred treated fumed silica is one wherein the fumed silica has been treated first with cyclic polysiloxanes, for example, dimethylcyclic tetramer, according to the methods as described in U.S. Pat. No. 2,938,009, and then treated with a silazane, for example, hexamethyldisilazane, as described in U.S. Pat. Nos. 3,635,743 and 3,847,848, so as to remove most of the free silanols on the surface of the tetramer treated silica. Removal of most of the free silanols refers to less than about 30% silanols remaining on the surface of the tetramer treated silica. Such a filler is sometimes referred to herein as "treated fumed silica".

The room temperature vulcanizable adhesive formulation of the present invention typically is prepared by homogeneously mixing (i.e. uniformly mixing) components (B)-(E) with the adhesion promoter (A) and any optional ingredients, using suitable batch, continuous, or semi-continuous mixing means, such as a spatula, a drum roller, a mechanical stirrer, a three-roll mill, a sigma blade mixer, a bread dough mixer, or a two-roll mill.

It is possible to mix all components in one mixing step immediately prior to the intended use of the curable composition. Alternatively, certain components can be pre-mixed to form two or more packages which can be stored, if desired, and then mixed in a final step immediately prior to the intended use thereof.

Preferably, the vinyl-containing polydiorganosiloxane (B) will be homogeneously mixed with a hydrosilylation catalyst (D) and any additional reinforcing filler to form a package (1). Package (2) will be a mixture of the hydrogen-containing polysiloxane (C), at least one vinyl-containing polydiorganosiloxane, and inhibitor. Package (2) is modified with adhesion promoter, (A), additional inhibitor, and additional hydrogen-containing polysiloxane. Package (1) and package (2) are then homogeneously mixed. Typically, the weight ratio of package (1) to package (2) is in a range between about 15:1 and about 1:1 and preferably, in a range between about 12:1 and about 1:1. These two packages can then be stored until the composition of the present invention is desired and then homogeneously mixed.

The thickness of the total composition on a substrate is typically in a range between about 20 millimeters and about 60 millimeters. The total composition of the present invention can be applied to the surface of a substrate by any suitable means such as rolling, spreading, spraying, and the like, and subsequently cured. After application of the total composition onto the substrate, the composition can be cured at room temperature over a period in a range between about 0.25 hours and about 150 hours. Typically, the cure temperature is in a range between about 25° C. and about 150° C.

When applied to a substrate, the total composition of the present invention has the desirable property of failing cohesively instead of adhesively when tested. A lap shear adhesion strength test is commonly used to measure adhesive failure and cohesive failure. "Adhesive failure" as used herein indicates that the silicone layer separates from the substrate at the point wherein the two layers meet, that is, the bond between the silicone layer and the substrate ruptures before the silicone layer or the substrate ruptures. "Cohesive failure" as used herein indicates that the silicone layer or the substrate ruptures before the bond between the silicone layer and the substrate fails.

The room temperature vulcanizable adhesive formulation has been found to cohesively bond on metal substrates, metal oxide substrates, and polymer substrates. Metal substrates include, but are not limited to, treated and untreated aluminum substrates and treated and untreated steel substrates. Polymer substrates include, but are not limited to phenolic resins, epoxy resins, polyetherimides, polyamides, unsaturated polyesters, poly(ethylene terephthalate), polycarbontes, polyphenylene sulfide, polyacetals, and polyimides. Preferably, the room temperature vulcanizable adhesive formulation is used for adhesion to phenolic resins, epoxy resins, and untreated metal substrates. Treating the substrate may include cleaning the substrate, applying a primer known to those skilled in the art, or a combination thereof. The compositions can be used as adhesives for applications in the military and laser industry as well as the electronic industry and automotive industry.

Room temperature vulcanizable adhesive formulations cure by mechanisms such as hydrosilylation or condensation. In order that those skilled in the art may better understand the practice of the present invention, the following examples of silicone compositions curing via hydrosilylation are given by way of illustration and not by way of limitation.

EXAMPLE 1

A 250 milliliter round-bottom flask was equipped with a reflux condenser, a stir bar, a nitrogen inlet, and charged with 100 grams diallylsuccinate (0.504 moles) and 30 parts per million Platinum (64.1 microliters ($\mu$l) of a 5% Karstedt's solution). The mixture was heated and stirred at 70° C. for 5 minutes after which time trimethoxysilane was slowly added (145 milliliters; 135 grams; 1.11 mol). The mixture was allowed to react for 24 hours after which time the excess trimethoxysilane was stripped in vacuo. A yield of 184 grams of bis(trimethoxysilylpropyl)succinate (84% yield) was obtained. The purity and identity of the product were determined by proton nuclear magnetic resonance spectroscopy (4.1 ppm 4H triplet, 3.5 ppm 18H singlet, 2.6 ppm 4H singlet, 1.8 ppm 4H multiplet, 0.6 ppm 4H triplet).

A silicone composition was prepared by adding varying amounts of $M^H_2Q$ resin, bis(trimethoxysilylpropyl)

succinate, and 2-methyl-3-butyn-2-ol (inhibitor) to modify 2 grams of package (2). Package (2) initially contained 47% by weight of a vinyl-terminated polydimethylsiloxane (0.06% by weight vinyl content; viscosity of 78,000 centipoise), 47.5% of a hydrogen-containing siloxane (0.8% by weight hydride content; viscosity of 40 centipoise), 3.8% by weight of methylvinyl tetramer inhibitor, and 0.1% by weight of 3,5 dimethyl-1-hexyn-3-ol. The modified package (2) was then combined with 20 grams of package (1) which contained 35 ppm of platinum catalyst, 40.4% of a silicone resin (1.26% by weight vinyl content; viscosity of 32,000 centipoise), 20.3% of a vinyl-terminated polydimethylsiloxane (0.06% by weight vinyl content; viscosity of 78,000 centipoise), 12% of a vinyl-terminated polydimethylsiloxane (0.17% by weight vinyl content; viscosity of 3,700 centipoise), and 27.6% silica filler. The modified package (2) and package (1) were mixed thoroughly and degassed under vacuum to provide a room temperature vulcanizable adhesive formulation. The room temperature vulcanizable adhesive formulation was applied to bare aluminum lap shear samples (one inch by four inches) with a one inch overlap. The specimens were cured at 6 days at room temperature. The lap shear adhesion strength was measured on an Instron 4202 instrument with a crosshead speed of 2 inches per minutes. The results of the varying amounts of bis (trimethoxysilylpropyl)succinate, additional hydrogen-containing polysiloxane, and inhibitor can be seen in Table 1.

TABLE 1

| Adhesion promoter (g) | $M^H_2Q$ resin (g) | Inhibitor (µl) | Test Results | Lap shear strength (psi) |
| --- | --- | --- | --- | --- |
| 0.17 | 0 | 2.5 | 100% cohesive failure | 595 +/−12 |
| 0.17 | 0 | 5 | 100% cohesive failure | 685 +/−25 |
| 0.27 | 0.15 | 5 | 100% cohesive failure | 547 +/−29 |
| 0.17 | 0.15 | 2.5 | 100% cohesive failure | 616 +/−13 |
| 0.22 | 0.075 | 3.75 | 100% cohesive failure | 544 +/−34 |
| 0.27 | 0 | 2.5 | 100% cohesive failure | 572 +/−58 |
| 0.17 | 0.15 | 5 | 100% cohesive failure | 647 +/−23 |
| 0.27 | 0.15 | 2.5 | Mixed mode | 616 +/−43 |
| 0.27 | 0 | 5 | 100% cohesive failure | 628 +/−29 |

As evident from the above-table, bis (trimethoxysilylpropyl)succinate is an effective adhesion promoter for adhesion to bare aluminum. "Mixed mode" as used herein refers to failure which was both adhesive and cohesive.

EXAMPLE 2

The method of Example 1 was used with a variation of adhesion promoter. Bis(trimethoxysilylpropyl) hydromuconate was used in place of bis (trimethoxysilylpropyl)succinate. Results of the varying amounts of bis(trimethoxysilylpropyl)hydromuconate, additional hydrogen-containing polysiloxane, and inhibitor can be seen in Table 2.

TABLE 2

| Adhesion promoter (g) | $M^H_2Q$ resin (g) | Inhibitor (µl) | Test Results | Lap shear strength (psi) |
| --- | --- | --- | --- | --- |
| 0.17 | 0 | 5 | 100% adhesive failure | 279 +/−77 |
| 0.17 | 0.15 | 5 | 100% adhesive failure | 353 +/−93 |
| 0.17 | 0 | 2.5 | 100% adhesive failure | 197 +/−43 |
| 0.27 | 0 | 2.5 | Mixed mode | 437 +/−98 |
| 0.27 | 0.15 | 2.5 | 100% adhesive failure | 176 +/−148 |

TABLE 2-continued

| Adhesion promoter (g) | $M^H_2Q$ resin (g) | Inhibitor (µl) | Test Results | Lap shear strength (psi) |
| --- | --- | --- | --- | --- |
| 0.27 | 0.15 | 5 | 100% adhesive failure | 390 +/−85 |
| 0.27 | 0 | 5 | Mixed mode | 407 +/−162 |
| 0.17 | 0.15 | 2.5 | 100% adhesive failure | 400 +/−106 |
| 0.22 | 0.075 | 3.75 | 100% adhesive failure | 270 +/−41 |

As the above table indicates, none of the samples provided 100% cohesive failure on bare aluminum.

These results indicate that bis(trimethoxysilylpropyl) succinate is an effective adhesion promoter when incorporated into the silicone formulations. Formulations with the bis(trimethoxysilylpropyl)succinate are capable of curing at room temperature and lap shear composites on bare aluminum fail cohesively within the silicone.

EXAMPLE 3

The method of Example 1 was used with a 0.1 grams bis(trimethoxysilylpropyl)succinate and 5 µl 2-methyl-3-butyn-2-ol. Lap shears were made to test the adhesion of the bis(trimethoxysilylpropyl)succinated formulation on aluminum-clad (alclad) aluminum, bare aluminum, anodized bare aluminum (sulfuric acid satin—clear anodization), and steel substrates. All samples were cured at room temperature for 6 days.

TABLE 3

| Substrate | Lap shear strength (psi) | Test Results |
| --- | --- | --- |
| Alclad aluminum | 634 +/−33 | 100% Cohesive failure |
| Bare aluminum | 598 +/−35 | 100% Cohesive failure |
| Steel | 567 +/−44 | 100% Cohesive failure |
| Anodized bare aluminum | 587 +/−20 | 80–100% Cohesive failure |

EXAMPLE 4

The bis(trimethoxysilylpropyl)succinate formulation of Example 3 was evaluated for adhesion to epoxy substrates using the peel method. Samples were cured for seven days prior to testing. In all cases, the failure was cohesive, with a lap shear strength mean value of 19.5+/−0.5 psi for samples of total thickness between 0.135–0.18 inches and a lap shear strength mean value of 15.7+/−1.5 psi for samples of total thickness between 0.25–0.31 inches.

EXAMPLE 5

Adhesion and lap shear strength were also evaluated on glass filled phenolic substrates using the bis (trimethoxysilylpropyl)succinate formulation of Example 3. Samples were cured in an oven at 100° C. for 1 hour. Cohesive failure was observed in all samples with a lap shear strength mean value of 14.5+/−1.0 psi for samples of total thickness 0.21–0.22 inches and a lap shear strength mean value of 18.7+/−0.6 psi for samples of total thickness 0.19–0.195 inches.

EXAMPLE 6

The method of Example 1 was used with a variation of adhesion promoter. Bis(trimethoxysilylpropyl)sebacate was used in place of bis(trimethoxysilylpropyl)succinate. Results of the varying amounts of bis (trimethoxysilylpropyl)sebacate, additional hydrogen-containing polysiloxane, and inhibitor can be seen in Table 4.

TABLE 4

| Adhesion promoter (g) | $M^H{}_2Q$ resin (g) | Inhibitor (μl) | Test Results | Lap shear strength (psi) |
| --- | --- | --- | --- | --- |
| 0.17 | 0 | 5 | 100% adhesive failure | 147 +/−31 |
| 0.17 | 0.15 | 5 | 100% adhesive failure | 83 +/−15 |
| 0.17 | 0 | 2.5 | 100% adhesive failure | 155 +/−46 |
| 0.27 | 0 | 2.5 | 85–100% adhesive failure | 295 +/−51 |
| 0.27 | 0.15 | 2.5 | No adhesion | |
| 0.27 | 0.15 | 5 | 100% adhesive failure | 154 +/−27 |
| 0.27 | 0 | 5 | 100% adhesive failure | 153 +/−24 |
| 0.17 | 0.15 | 2.5 | 100% adhesive failure | 76 +/−57 |
| 0.22 | 0.075 | 3.75 | 100% adhesive failure | 103 +/−41 |
| 0.22 | 0.075 | 3.75 | 100% adhesive failure | 108 +/−45 |

EXAMPLE 7

The method of Example 1 was used with a variation of adhesion promoter. Bis(trimethoxysilylpropyl)adipate was used in place of bis(trimethoxysilylpropyl)succinate. Results of the varying amounts of bis(trimethoxysilylpropyl)adipate, additional hydrogen-containing polysiloxane, and inhibitor can be seen in Table 5.

TABLE 5

| Adhesion promoter (g) | $M^H{}_2Q$ resin (g) | Inhibitor (μl) | Test Results | Lap shear strength (psi) |
| --- | --- | --- | --- | --- |
| 0.17 | 0 | 5 | 80–100% adhesive failure | 378 +/−93 |
| 0.17 | 0.15 | 5 | 80–100% adhesive failure | 425 +/−65 |
| 0.17 | 0 | 2.5 | Mixed mode-100% adhesive failure | 566 +/−94 |
| 0.27 | 0 | 2.5 | Mixed mode-90% adhesive failure | 506 +/−86 |
| 0.27 | 0.15 | 2.5 | 80–100% adhesive failure | 283 +/−71 |
| 0.27 | 0.15 | 5 | Mixed mode-70% adhesive failure | 493 +/−50 |
| 0.27 | 0 | 5 | Mixed mode-100% adhesive failure | 391 +/−23 |
| 0.17 | 0.15 | 2.5 | No adhesion | |
| 0.22 | 0.075 | 3.75 | Mixed mode-100% adhesive failure | 552 +/−48 |
| 0.22 | 0.075 | 3.75 | No adhesion | |

As seen in Table 4 and 5, no samples with bis(trimethoxysilylpropyl)sebacate or bis(trimethoxysilylpropyl)adipate provided cohesive failure on aluminum-clad aluminum or bare aluminum substrates.

While typical embodiments have been set forth for the purpose of illustration, the foregoing descriptions should not be deemed to be a limitation on the scope of the invention. Accordingly, various modifications, adaptations, and alternatives may occur to one skilled in the art without departing from the spirit and scope of the present invention.

What is claimed is:

1. A silicone composition comprising a room temperature vulcanizable adhesive formulation which comprises:

(A) at least one bis(trialkoxysilylalkyl)succinate, (B) a vinyl-containing polydiorganosiloxane, (C) a hydrogen-containing polysiloxane, and (D) a catalytic amount of a hydrosilylation catalyst.

2. The composition in accordance with claim 1, wherein the room temperature vulcanizable adhesive formulation further comprises an extending filler (E), a reinforcing filler (F), or combination thereof.

3. The composition in accordance with claim 1, wherein the vinyl-containing polydiorganosiloxane comprises a vinyl-containing polydiorganosiloxane having a general formula, $$(R^4)_2R^5SiO[(R^4)_2SiO]_m[R^4R^5SiO]_nSi(R^4)_2R^5$$

wherein

R$^5$ is a vinyl radical, R$^4$ is selected from the group consisting of alkyl radicals having carbon atoms in a range between about 1 and about 8, phenyl radicals, fluoroalkyl radicals, having carbon atoms in a range between about 3 and about 10 and mixtures thereof, "m"+"n" has a value sufficient to provide a total polydiorganosiloxane viscosity in a range between about 100 centipoise and about 100,000 centipoise at 25° C., and a vinyl content in a range between about 0.02% by weight and about 2.0% by weight of the vinyl-containing polydiorganosiloxane, and a vinyl-containing silicone resin copolymer in a range between about 0% by weight and about 70% by weight of the total composition having, $$(R^6)_3SiO_{1/2} \text{ units and } SiO_{4/2} \text{ units,}$$

wherein R$^6$ is a vinyl radical, or a monovalent hydrocarbon radical free of aliphatic unsaturation and containing no more than six carbon atoms, the ratio of $(R^6)_3SiO_{1/2}$ units to $SiO_{4/2}$ units being in a range between about 0.5:1 and about 1.5:1, and the resin having a vinyl content in a range between about 1.5% by weight and about 3.5% by weight of the vinyl-containing siloxane resin copolymer.

4. The composition in accordance with claim 1, wherein the vinyl-containing polydiorganosiloxane is present in a range between about 10% by weight and about 50% by weight of the total composition.

5. The composition in accordance with claim 1, wherein the hydrogen-containing polysiloxane has an average unit formula, $$R^7{}_dH_eSiO_{(4-d-e)/2}$$

wherein R$^7$ is a hydrogen, a monovalent hydrocarbon radical, or a halogenated monovalent hydrocarbon radical having carbon atoms in a range between about 1 and about 10 and free of aliphatic unsaturation, "d" has a value in a range between 0 and about 3, "e" has a value in a range between about 1 and about 3, and the sum of "d"+"e" has a value in a range between about 1 and about 3.

6. The composition in accordance with claim 1, wherein the hydrogen-containing polysiloxane is present in a range between about 1% by weight and about 15% by weight of the total composition.

7. The composition in accordance with claim 1, wherein the bis(trialkoxysilylalkyl)succinate has a formula $$(R^3O)_3Si(CR^1{}_2)_xOC(CR^2{}_2)_2CO(CR^1{}_2)_xSi(OR^3);$$

wherein each R$^3$ independently represents an alkyl radical comprising carbon atoms in a range between about 1 and about 20; R$^1$ represents hydrogen; R$^2$ represents hydrogen or an alkyl radical comprising carbon atoms in a range between about 1 and about 20; and "x" is in a range between about 3 and about 8.

8. The composition in accordance with claim 7, wherein $R^3$ is an alkyl radical comprising one carbon atom; $R^2$ is hydrogen; and "x" is 3.

9. The composition in accordance with claim 1, wherein the bis(trialkoxysilylalkyl)succinate is present in a range between about 0.1% by weight and about 5% by weight of the total composition.

10. The composition in accordance with claim 2, wherein the extending filler is present in a range between about 0% by weight and about 50% by weight of the total composition.

11. The composition in accordance with claim 2, wherein the reinforcing filler is present in a range between about 0% by weight and about 70% by weight of the total composition.

12. An article comprising a metal substrate treated with the composition of claim 1.

13. The article in accordance with claim 12, wherein the substrate comprises aluminum.

14. An article comprising a polymer substrate treated with the composition of claim 1.

15. The article in accordance with claim 14, wherein the substrate comprises an epoxy resin or a phenolic resin.

16. A silicone composition comprising a room temperature vulcanizable adhesive formulation which composition comprises
(A) at least one bis(trimethoxysilylpropyl)succinate present in a range between about 0.1% by weight and about 5% by weight of the total composition;
(B) a vinyl-containing polydiorganosiloxane present in a range between about 10% by weight and about 50% by weight of the total composition,
(C) a hydrogen-containing polysiloxane in a range between about 1% by weight and about 15% by weight of the total composition,
(D) a catalytic amount of a hydrosilylation catalyst,
(E) an extending filler in a range between about 0% by weight and about 50% by weight of the total composition,
(F) a reinforcing filler in a range between about 0% by weight and about 70% by weight of the total composition.

17. An article comprising a metal substrate treated with the composition of claim 16.

18. The article in accordance with claim 17, wherein the substrate comprises aluminum.

19. An article comprising a polymer substrate treated with the composition of claim 16.

20. The article in accordance with claim 19, wherein the substrate comprises an epoxy resin or a phenolic resin.

21. A method to provide cohesive failure to a silicone composition and a substrate which comprises the steps of:
(I) applying a silicone composition to a substrate wherein the silicone composition comprises:
(E) at least one bis(trialkoxysilylalkyl)succinate,
(F) a vinyl-containing polydiorganosiloxane,
(G) a hydrogen-containing polysiloxane, and
(H) a catalytic amount of a hydrosilylation catalyst, and
(II) curing the silicone composition.

22. The method in accordance with claim 21, wherein the silicone composition further comprises an extending filler (E), a reinforcing filler (F), or combinations thereof.

23. The method in accordance with claim 22, wherein the vinyl-containing polydiorganosiloxane comprises a vinyl-containing polydiorganosiloxane having a general formula,

wherein
$R^5$ is a vinyl radical, $R^4$ is selected from the group consisting of alkyl radicals having carbon atoms in a range between about 1 and about 8, phenyl radicals, fluoroalkyl radicals having carbon atoms in a range between about 3 and about 10 and mixtures thereof, "m"+"n" has a value sufficient to provide a total vinyl-containing composition with a viscosity in a range between about 100 centipoise and about 100,000 centipoise at 25° C., and a vinyl content in a range between about 0.02% by weight and about 2.0% by weight of the vinyl-containing polydiorganosiloxane, and
a vinyl-containing siloxane resin copolymer in a range between about 0% by weight and about 70% by weight of the total composition having,

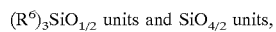

wherein $R^6$ is a vinyl radical, or a monovalent hydrocarbon radical free of aliphatic unsaturation and containing no more than six carbon atoms, the ratio of $(R^6)_3SiO_{1/2}$ units to $SiO_{4/2}$ units being in a range between about 0.5:1 and about 1.5:1, and the resin having a vinyl content in a range between about 1.5% by weight and about 3.5% by weight of the vinyl-containing siloxane resin copolymer.

24. The method in accordance with claim 23, wherein the vinyl-containing polydiorganosiloxane is present in a range between about 10% by weight and about 50% by weight of the total composition.

25. The method in accordance with claim 21, wherein the hydrogen-containing polysiloxane comprises an average unit formula,

wherein $R^7$ is a hydrogen, a monovalent hydrocarbon radical, or a halogenated monovalent hydrocarbon radical having carbon atoms in a range between about 1 and about 10 and free of aliphatic unsaturation, "d" has a value in a range between 0 and about 3, "e" has a value in a range between about 1 and about 3, and the sum of "d"+"e" has a value in a range between about 1 and about 3.

26. The method in accordance with claim 21, wherein the hydrogen-containing polysiloxane is present in a range between about 1% by weight and about 15% by weight of the total composition.

27. The method in accordance with claim 21, wherein the bis(trialkoxysilylalkyl)succinate comprises a formula

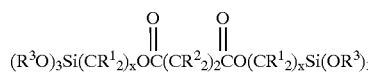

wherein each $R^3$ independently represents an alkyl radical comprising carbon atoms in a range between about 1 and about 20; $R^1$ represents hydrogen; $R^2$ represents hydrogen or an alkyl radical comprising carbon atoms in a range between about 1 and about 20; and "x" is in a range between about 3 and about 8.

28. The method in accordance with claim 27, wherein $R^3$ is an alkyl radical comprising one carbon atom; $R^2$ is hydrogen; and "x" is 3.

29. The method in accordance with claim 21, wherein the bis(trialkoxysilylalkyl)succinate is present in a range between about 0.1% by weight and about 5% by weight of the total composition.

30. The method in accordance with claim 21, wherein the substrate comprises a metal.

31. The method in accordance with claim 30, wherein the metal comprises aluminum.

32. The method in accordance with claim 21, wherein the substrate comprises a polymer.

33. The method in accordance with claim 32, wherein the polymer comprises an epoxy resin or a phenolic resin.

34. The method in accordance with claim 21, wherein the silicone composition is applied to a thickness in a range between about 20 millimeters and about 60 millimeters.

35. The method in accordance with claim 21, wherein the silicone composition is cured at a temperature in a range between about 25° C. and about 150° C. over a period in a range between about 0.25 hours and about 150 hours.

36. A method to provide cohesive failure to a silicone composition and an aluminum substrate which comprises the steps of:
   (1) applying a silicone composition to a substrate to a thickness in a range between about 20 millimeters and about 60 millimeters, wherein the silicone composition comprises:
      (A) a bis(trimethoxysilylpropyl)succinate present in a range between about 0.1% by weight and about 5% by weight of the total composition;
      (B) a vinyl-containing polydiorganosiloxane present in a range between about 10% by weight and about 50% by weight of the total composition,
      (C) a hydrogen-containing polysiloxane in a range between about 1% by weight and about 15% by weight of the total composition,
      (D) a catalytic amount of a hydrosilylation catalyst,
      (E) an extending filler in a range between about 0% by weight and about 50% by weight of the total composition,
      (F) a reinforcing filler in a range between about 0% by weight and about 70% by weight of the total composition, and
   (2) curing the silicone composition at a temperature in a range between about 25° C. and about 150° C. over a period in a range between about 0.25 hours and about 150 hours.

37. A method to provide cohesive failure to a silicone composition and a phenolic resin substrate which comprises the steps of:
   (1) applying a silicone composition to a substrate to a thickness in a range between about 20 millimeters and about 60 millimeters, wherein the silicone composition comprises:
      (A) a bis(trimethoxysilylpropyl)succinate present in a range between about 0.1% by weight and about 5% by weight of the total composition;
      (B) a vinyl-containing polydiorganosiloxane present in a range between about 10% by weight and about 50% by weight of the total composition,
      (C) a hydrogen-containing polysiloxane in a range between about 1% by weight and about 15% by weight of the total composition,
      (D) a catalytic amount of a hydrosilylation catalyst,
      (E) an extending filler in a range between about 0% by weight and about 50% by weight of the total composition,
      (F) a reinforcing filler in a range between about 0% by weight and about 70% by weight of the total composition, and
   (2) curing the silicone composition at a temperature in a range between about 25° C. and about 150° C. over a period in a range between about 0.25 hours and about 150 hours.

38. A method to provide cohesive failure to a silicone composition and an epoxy resin substrate which comprises the steps of:
   (1) applying a silicone composition to a substrate to a thickness in a range between about 20 millimeters and about 60 millimeters, wherein the silicone composition comprises:
      (A) a bis(trimethoxysilylpropyl)succinate present in a range between about 0.1% by weight and about 5% by weight of the total composition;
      (B) a vinyl-containing polydiorganosiloxane present in a range between about 10% by weight and about 50% by weight of the total composition,
      (C) a hydrogen-containing polysiloxane in a range between about 1% by weight and about 15% by weight of the total composition,
      (D) a catalytic amount of a hydrosilylation catalyst,
      (E) an extending filler in a range between about 0% by weight and about 50% by weight of the total composition,
      (F) a reinforcing filler in a range between about 0% by weight and about 70% by weight of the total composition, and
   (2) curing the silicone composition at a temperature in a range between about 25° C. and about 150° C. over a period in a range between about 0.25 hours and about 150 hours.

* * * * *